(12) United States Patent
Pan et al.

(10) Patent No.: US 12,369,820 B2
(45) Date of Patent: Jul. 29, 2025

(54) USER IDENTIFICATION METHOD USING ELECTROCARDIOGRAM AND ELECTROMYOGRAM

(71) Applicant: Industry-Academic Cooperation Foundation, Chosun University, Gwangju (KR)

(72) Inventors: Sungbum Pan, Gwangju (KR); Gyuho Choi, Gwangju (KR)

(73) Assignee: Industry-Academic Cooperation Foundation, Chosun University, Gwangju (KR)

( * ) Notice: Subject to any disclaimer, the term of this patent is extended or adjusted under 35 U.S.C. 154(b) by 420 days.

(21) Appl. No.: 17/816,190

(22) Filed: Jul. 29, 2022

(65) Prior Publication Data
US 2023/0309864 A1    Oct. 5, 2023

(30) Foreign Application Priority Data
Apr. 5, 2022    (KR) .......................... 10-2022-0042244

(51) Int. Cl.
*A61B 5/117*    (2016.01)
*A61B 5/00*     (2006.01)
*A61B 5/318*    (2021.01)
*A61B 5/389*    (2021.01)

(52) U.S. Cl.
CPC .............. *A61B 5/117* (2013.01); *A61B 5/318* (2021.01); *A61B 5/389* (2021.01); *A61B 5/6893* (2013.01); *A61B 5/7207* (2013.01); *A61B 5/7253* (2013.01)

(58) Field of Classification Search
CPC ........ G06V 20/59; G06V 20/56; G06V 40/23; G06V 40/70; G06V 10/454; G06V 10/469; G06V 10/774; G06V 10/82; B60K 28/06; H04W 4/02; A61B 5/117; A61B 5/318; A61B 5/389; A61B 5/6893; A61B 5/7207; A61B 5/7253; A61B 5/7264; A61B 5/346; A61B 5/397; B60R 25/01; B60R 25/25; G06N 3/09; G06T 7/11; G06T 11/00
See application file for complete search history.

(56) References Cited

U.S. PATENT DOCUMENTS

| | | | |
|---|---|---|---|
| 9,106,623 B2 * | 8/2015 | Paddon | H04W 4/90 |
| 9,642,577 B1 * | 5/2017 | Li | A61B 5/366 |
| 10,095,229 B2 * | 10/2018 | Myers | G06V 20/59 |
| 10,432,581 B2 * | 10/2019 | Field | H04L 61/5061 |
| 2013/0160082 A1 * | 6/2013 | Miller | H04L 67/14 |
| | | | 709/227 |

* cited by examiner

*Primary Examiner* — Wassim Mahrouka
(74) *Attorney, Agent, or Firm* — Studebaker Brackett PLLC

(57) ABSTRACT

Provided is a method of identifying a user by converting an electrocardiogram (ECG) and an electromyogram (EMG) into images, respectively, and inputting each converted image to a multi-stream convolutional neural network (multi-stream CNN). According to an embodiment of the present disclosure, the user identification method using the ECG and the EMG includes acquiring one-dimensional ECG and EMG signals for a user, converting the ECG and EMG signals into two-dimensional images, respectively, and identifying a user by inputting the two-dimensional images to a multi-stream convolutional neural network (multi-stream CNN), respectively.

12 Claims, 10 Drawing Sheets

FIG. 3
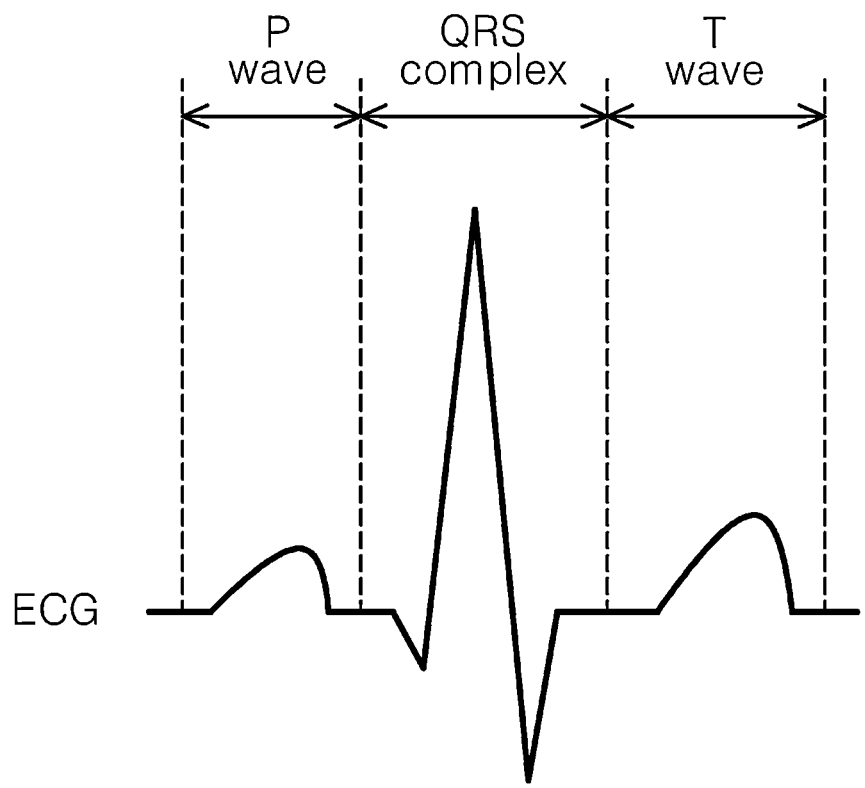
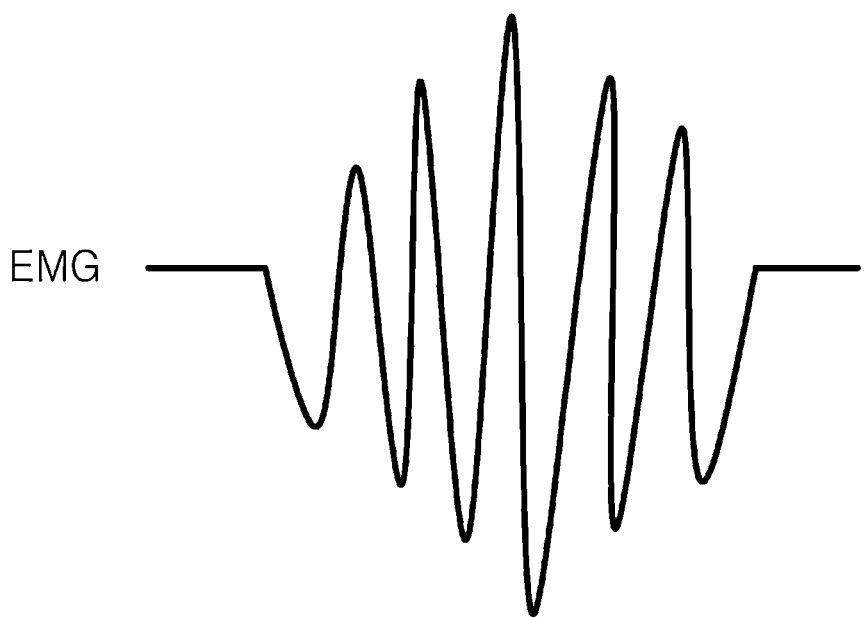

FIG. 6
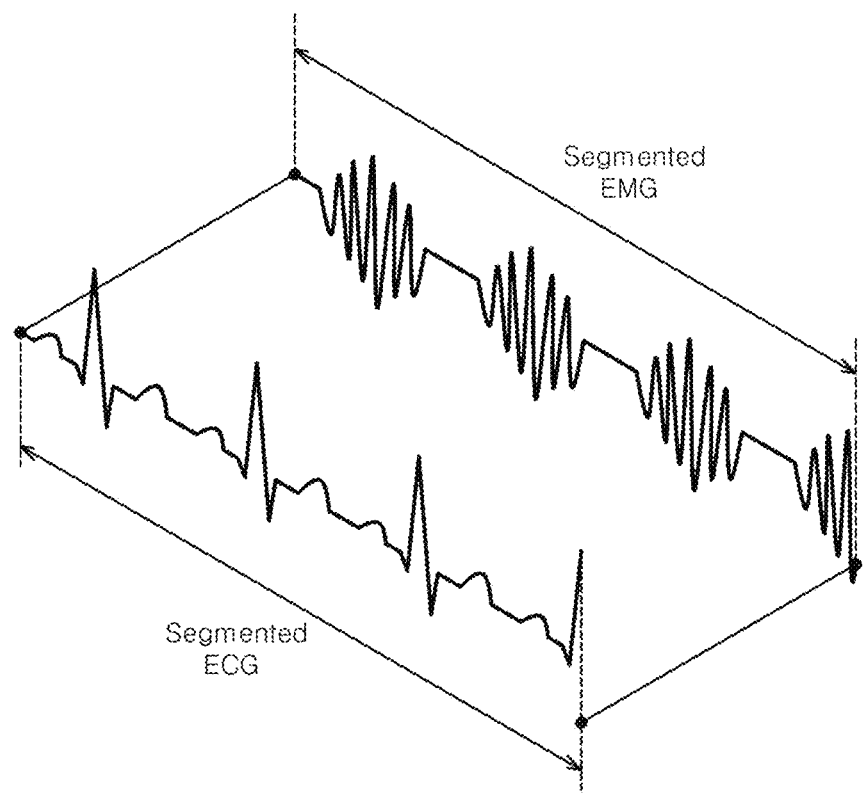
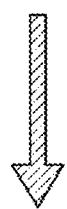 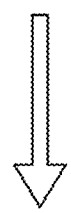
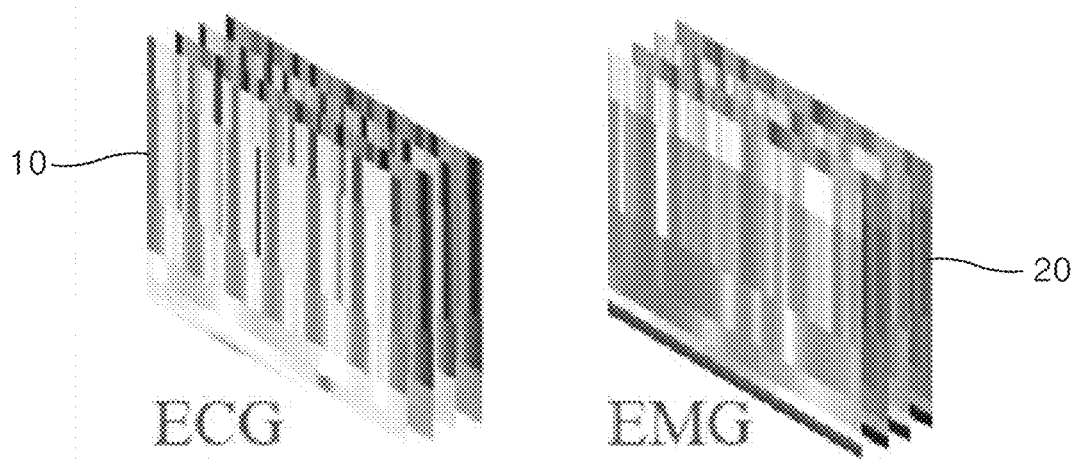

USER IDENTIFICATION METHOD USING ELECTROCARDIOGRAM AND ELECTROMYOGRAM

CROSS-REFERENCE TO RELATED APPLICATIONS

This application claims the priority of Korean Patent Application No. 10-2022-0042244 filed on Apr. 5, 2022, in the Korean Intellectual Property Office, the disclosure of which is incorporated herein by reference.

BACKGROUND OF THE INVENTION

Field of the Invention

The present disclosure relates to a method of identifying a user by converting an electrocardiogram and an electromyogram into images, respectively, and inputting each converted image to a multi-stream convolutional neural network.

Description of the Related Art

An electrocardiogram (ECG) has attracted attention as a biosignal for user identification by including unique characteristics of an individual according to electrophysiological factors of the heart and the location, size, physical conditions, and the like of the heart.

Accordingly, a user identification algorithm using the ECG has recently been developed, but since the ECG includes noise according to a user's physical condition, there is a limitation in that the identification accuracy is low. Specifically, the ECG includes motion artifacts caused by a user's action, and errors in an identification operation using the ECG frequently occur due to such noise.

Accordingly, there is a need for a method capable of improving detection accuracy by reflecting the user's behavioral characteristics in the identification operation through the user's ECG.

The above-described technical configuration is the background art for helping in the understanding of the present invention, and does not mean a conventional technology widely known in the art to which the present invention pertains.

SUMMARY OF THE INVENTION

An object of the present disclosure is to convert one-dimensional ECG and EMG signals into two-dimensional images, respectively, and identify a user based on features extracted from each image.

The objects of the present disclosure are not limited to the above-mentioned objects, and other objects and advantages of the present disclosure, which are not mentioned, will be understood through the following description, and will become apparent from the embodiments of the present disclosure. In addition, it will be appreciated that the objects and advantages of the present disclosure will be easily realized by those skilled in the art based on the appended claims and a combination thereof.

According to an aspect of the present disclosure, there is provided a user identification method using an electrocardiogram and an electromyogram including acquiring one-dimensional electrocardiogram (ECG) and electromyogram (EMG) signals for a user, converting the ECG and EMG signals into two-dimensional images, respectively, and identifying a user by inputting the two-dimensional images to a multi-stream convolutional neural network (multi-stream CNN), respectively.

In the embodiment, the acquiring of the one-dimensional ECG and EMG signals may include acquiring the ECG and EMG signals from a sensor in a vehicle coming into contact with a user's body.

In the embodiment, the converting of the ECG and EMG signals into the two-dimensional images, respectively may include normalizing the ECG signal and the EMG signal at the same sampling rate, and converting the normalized ECG signal and EMG signal into the two-dimensional images, respectively.

In the embodiment, the converting of the ECG and EMG signals into the two-dimensional images, respectively may include removing noise in the ECG and EMG signals through a Butterworth filter, and converting the noise-removed ECG signal and EMG signal into the two-dimensional images, respectively.

In the embodiment, the converting of the ECG and EMG signals into the two-dimensional images, respectively may include segmenting the ECG signal and the EMG signal by a preset time through non-fiducial segmentation, and converting the segmented ECG signal and EMG signal into the two-dimensional images, respectively.

In the embodiment, the converting of the ECG and EMG signals into the two-dimensional images, respectively may include converting ECG and EMG signals expressed in amplitudes to the time into two-dimensional images expressed by a time axis and a frequency axis, respectively.

In the embodiment, the converting of the ECG and EMG signals into the two-dimensional images, respectively may include converting the ECG and EMG signals into two-dimensional spectrograms.

In the embodiment, the converting of the ECG and EMG signals into the two-dimensional images, respectively may include converting the ECG and EMG signals into two-dimensional spectrograms by applying constant Q-transform (CQT) to the ECG and EMG signals.

In the embodiment, the converting of the ECG and EMG signals into the two-dimensional spectrograms, respectively may include converting the ECG and EMG signals into spectrograms according to Equation 1 below:

$$X(l, \omega) = \int_{-\infty}^{\infty} w(t, \omega) x(t + lM) e^{-i2\pi Qt} dt \quad \text{[Equation 1]}$$

(x represents a spectrogram value, ω represents each frequency, l represents a time index, w represents a window function, x represents an ECG or EMG signal, Q represents a quality factor, and M represents the number of frames to which a window is applied in the ECG or EMG signal)

In the embodiment, the multi-stream CNN may be supervised-learned by a training dataset using images of the ECG and EMG signals as input data and using the user identification information as label data.

In the embodiment, the inputting of the two-dimensional images to the multi-stream CNN may include inputting an image for the ECG signal to a first stream neural network, and inputting an image for the EMG signal to a second stream neural network.

In the embodiment, the identifying of the user may include concatenating features extracted from the first and second stream neural networks, respectively, and identifying the user based on the concatenated features.

In the embodiment, the concatenating of the extracted features may include element-wise summing the feature vector extracted from the first stream neural network and the feature vector extracted from the second stream neural network.

According to the present disclosure, by identifying the user based on features extracted from two-dimensional images corresponding to the ECG and EMG signals, respectively, it is possible to consider not only user's unique biometric information but also motion artifacts, thereby improving the accuracy of user identification.

Further, by converting the ECG and EMG signals into spectrograms through constant Q-transform (CQT) and identifying a user based thereon, it is possible to actively reflect morphological features of the ECG and EMG signals to neural network learning, thereby improving the accuracy of user identification.

In addition to the above-described effects, specific effects of the present disclosure will be described together with explanation of specific matters for carrying out the present disclosure.

BRIEF DESCRIPTION OF THE DRAWINGS

The above and other aspects, features and other advantages of the present invention will be more clearly understood from the following detailed description taken in conjunction with the accompanying drawings, in which:

FIG. 3 is a diagram illustrating ECG and EMG signals.

FIG. 6 is a diagram illustrating a state in which an ECG signal and an EMG signal are converted into two-dimensional images, respectively;

DETAILED DESCRIPTION OF THE PREFERRED EMBODIMENT

Figure 1:
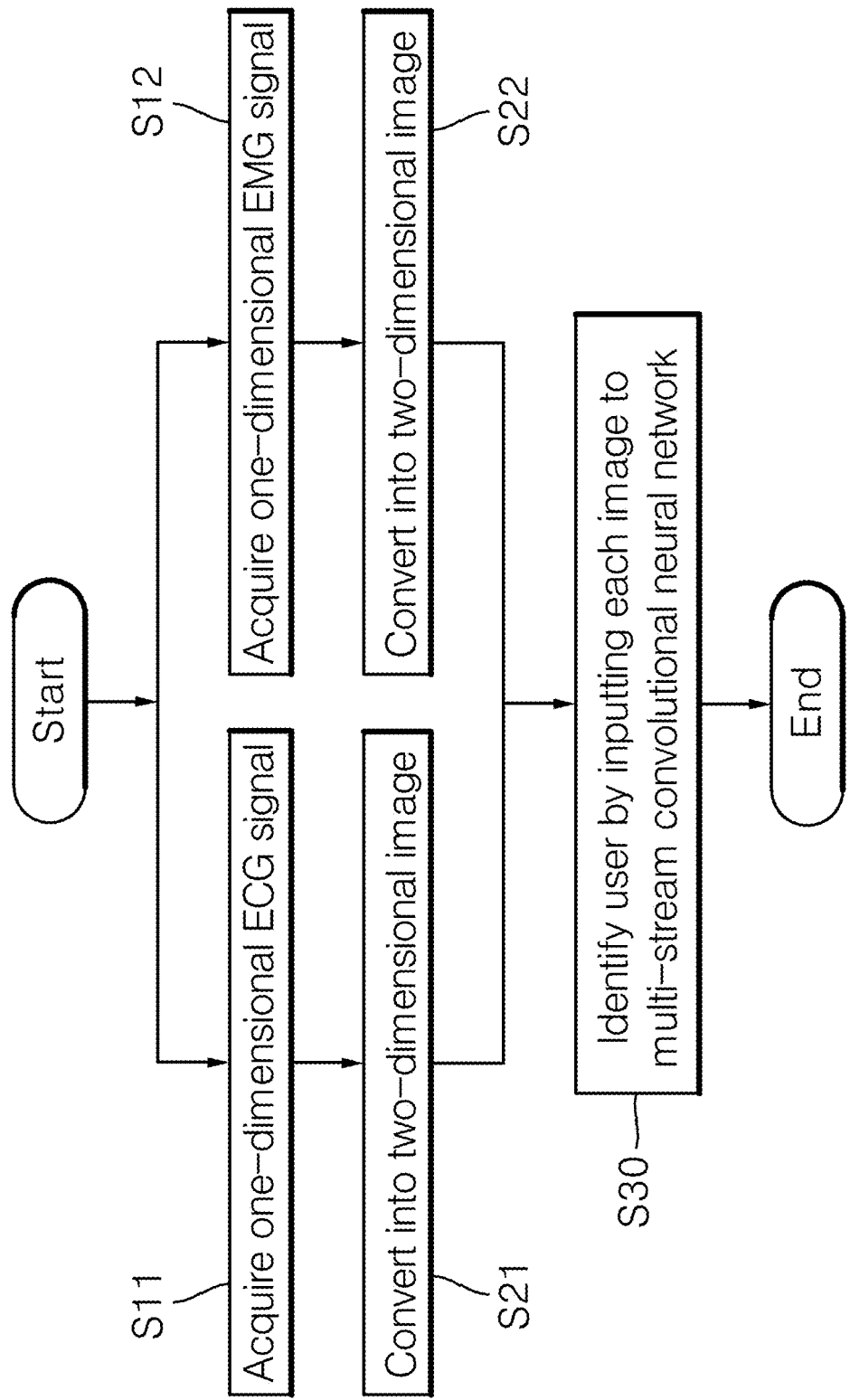
FIG. 1 is a flowchart illustrating a user identification method using an electrocardiogram (ECG) and an electromyogram (EMG) according to an embodiment of the present disclosure.

The above-described objects, features and advantages will be described below in detail with reference to the accompanying drawings, and accordingly, those of ordinary skill in the art to which the present disclosure pertains will be able to easily implement the technical idea of the present disclosure. In describing the present disclosure, a detailed description of related known technologies will be omitted if it is determined that they unnecessarily make the gist of the present disclosure unclear. Hereinafter, preferred exemplary embodiments of the present disclosure will be described in detail with reference to the accompanying drawings. In the drawings, like reference numerals are used to indicate like or similar components.

Although the terms "first", "second", and the like are used for describing various components, these components are not confined by these terms. These terms are used to distinguish only one component from other components, and unless otherwise described to the contrary, of course, a first component may be a second component.

In addition, when a component is described as being "connected", "coupled" or "accessed" to another component, it will be understood that the components may be directly connected or accessed to each other, but other components are "interposed" between the components, or each component may be "connected", "coupled" or "accessed" through other components.

Further, a singular form used in the present specification may include a plural form if there is no clearly opposite meaning in the context. In this specification, the term such as "comprising" or "including" should not be interpreted as necessarily including all various components or various steps disclosed in the specification, and it should be interpreted that some component or some steps among them may not be included or additional components or steps may be further included.

Throughout this specification, unless otherwise described to the contrary, "A and/or B" means A, B, or A and B, and unless otherwise described to the contrary, "C to D" means C or more and D or less.

The present disclosure relates to a method of identifying a user by converting an electrocardiogram (ECG) and an electromyogram (EMG) into images, respectively, and inputting each converted image to a multi-stream convolutional neural network (multi-stream CNN). Hereinafter, a user identification method using an electrocardiogram (ECG) and an electromyogram (EMG) according to an embodiment of the present disclosure will be described in detail with reference to FIGS. 1 to 9.

FIG. 1 is a flowchart illustrating a user identification method using an electrocardiogram (ECG) and an electromyogram (EMG) according to an embodiment of the present disclosure.

Figure 2:
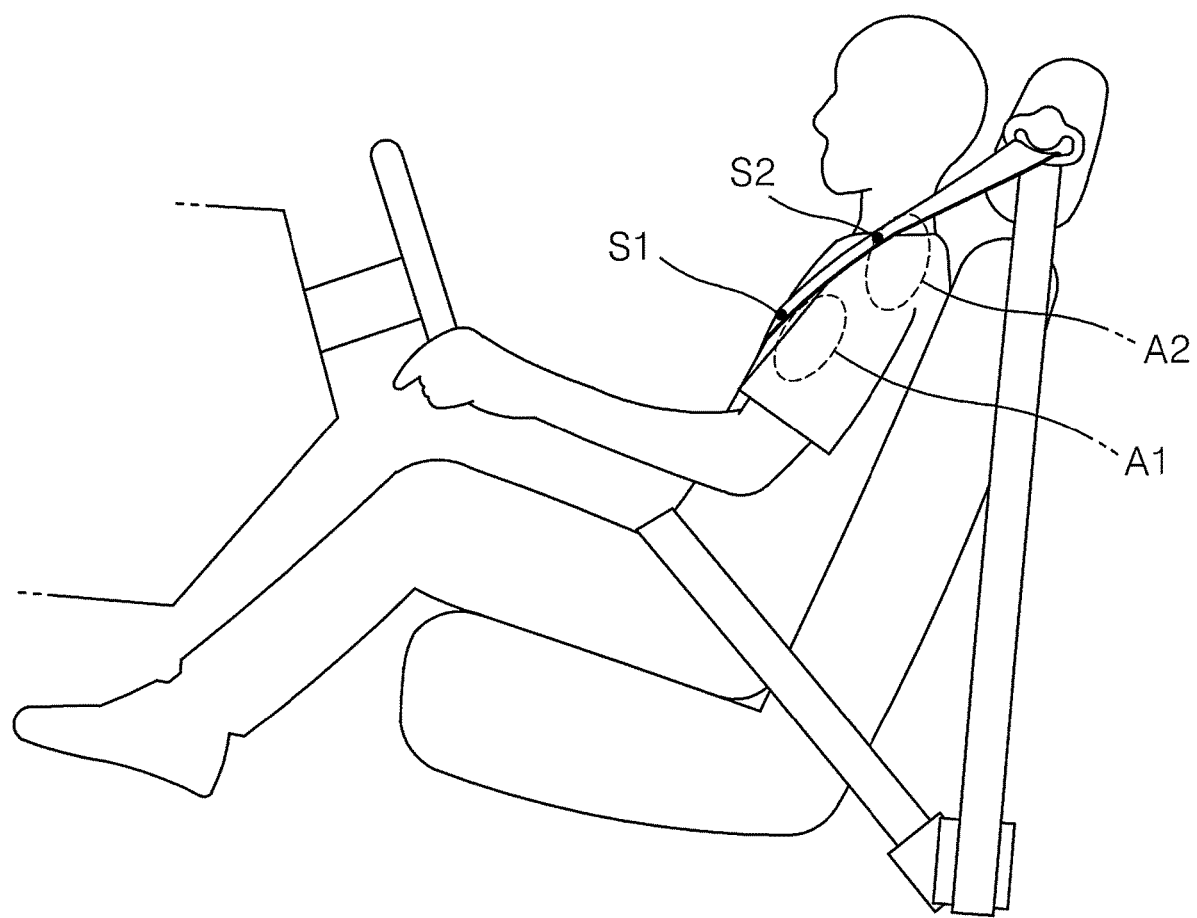
FIG. 2 is a diagram for describing sensors for detecting an ECG and an EMG, respectively.

FIG. 2 is a diagram for describing sensors for detecting an ECG and an EMG, respectively, and FIG. 3 is a diagram illustrating ECG and EMG signals.

Figure 4:
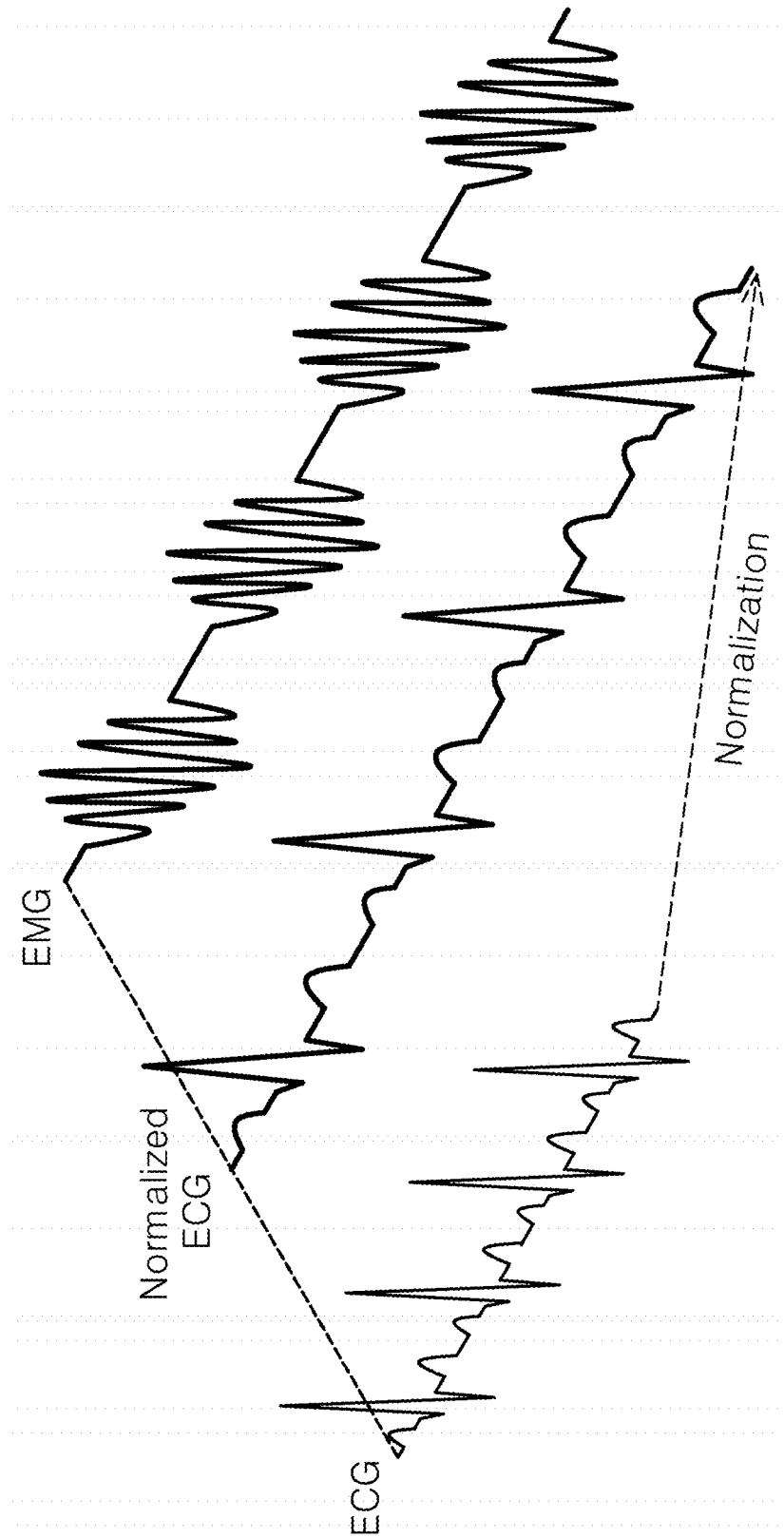
FIG. 4 is a diagram for describing a process of normalizing an ECG signal and an EMG signal.
Figure 5:
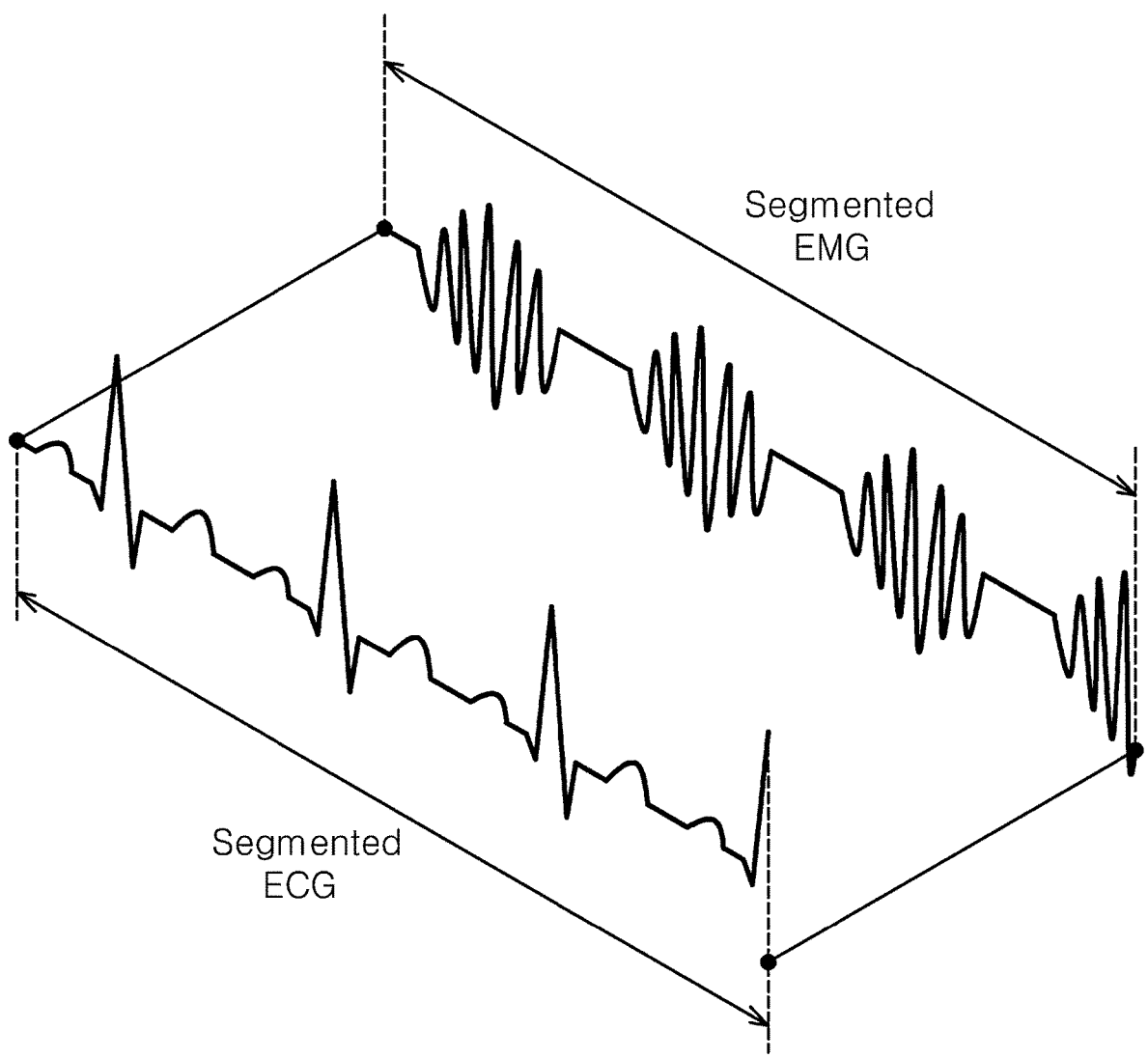
FIG. 5 is a diagram for describing a process of segmenting an ECG signal and an EMG signal.

FIG. 4 is a diagram for describing a process of normalizing an ECG signal and an EMG signal, FIG. 5 is a diagram for describing a process of segmenting an ECG signal and an EMG signal, and FIG. 6 is a diagram illustrating a state in which an ECG signal and an EMG signal are converted into two-dimensional images, respectively.

Figure 7:
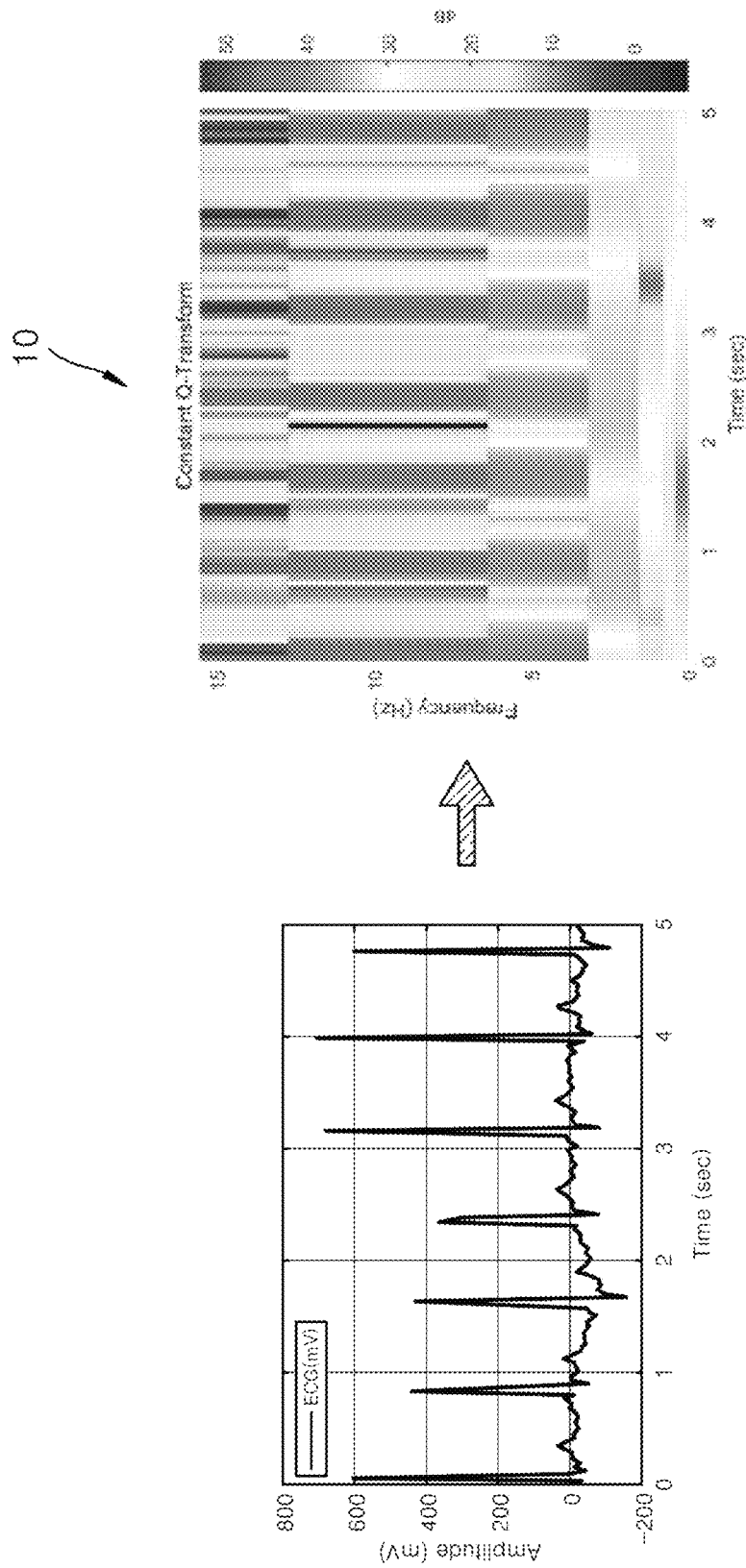
FIGS. 7 and 8 are diagrams illustrating a state in which an ECG signal and an EMG signal are converted into CQT images, respectively.
Figure 8:
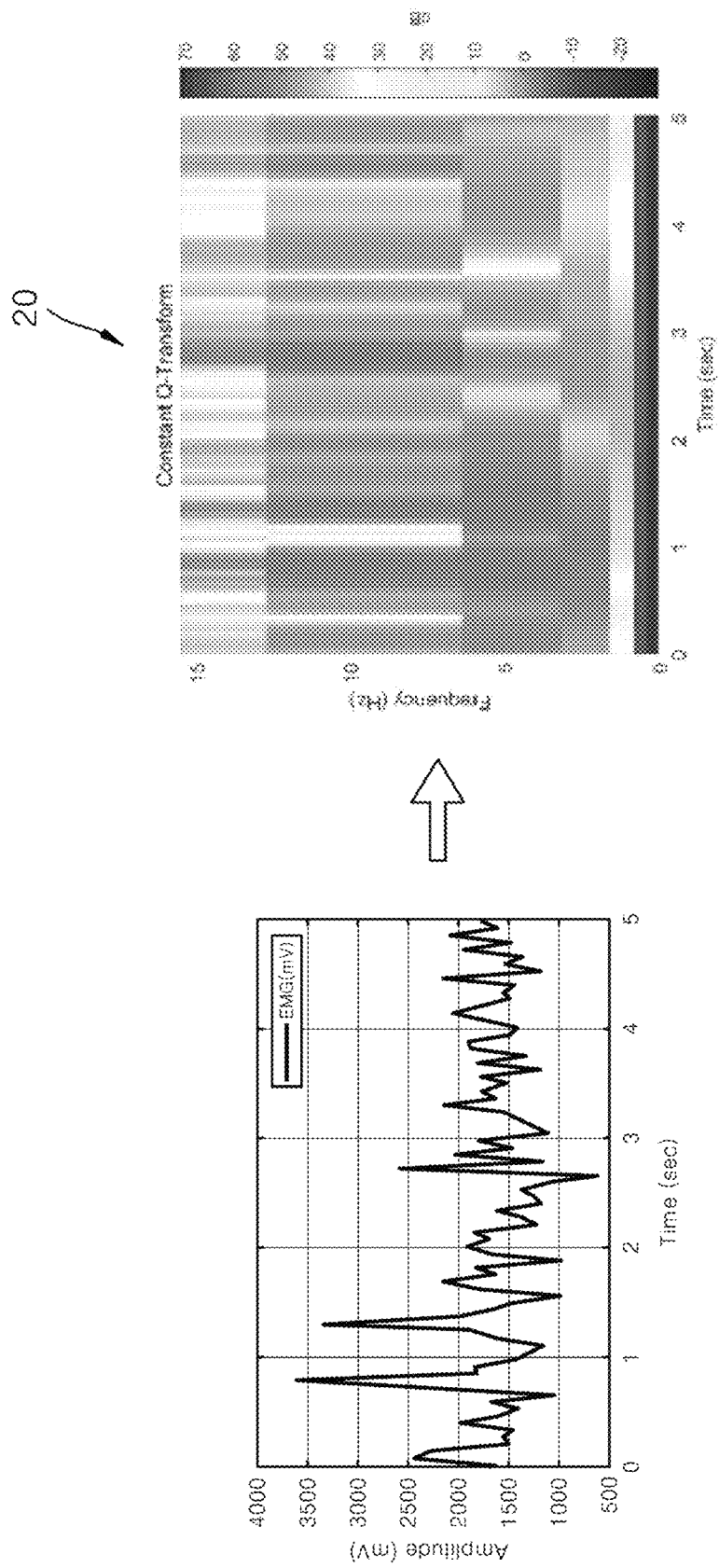
Figure 9:
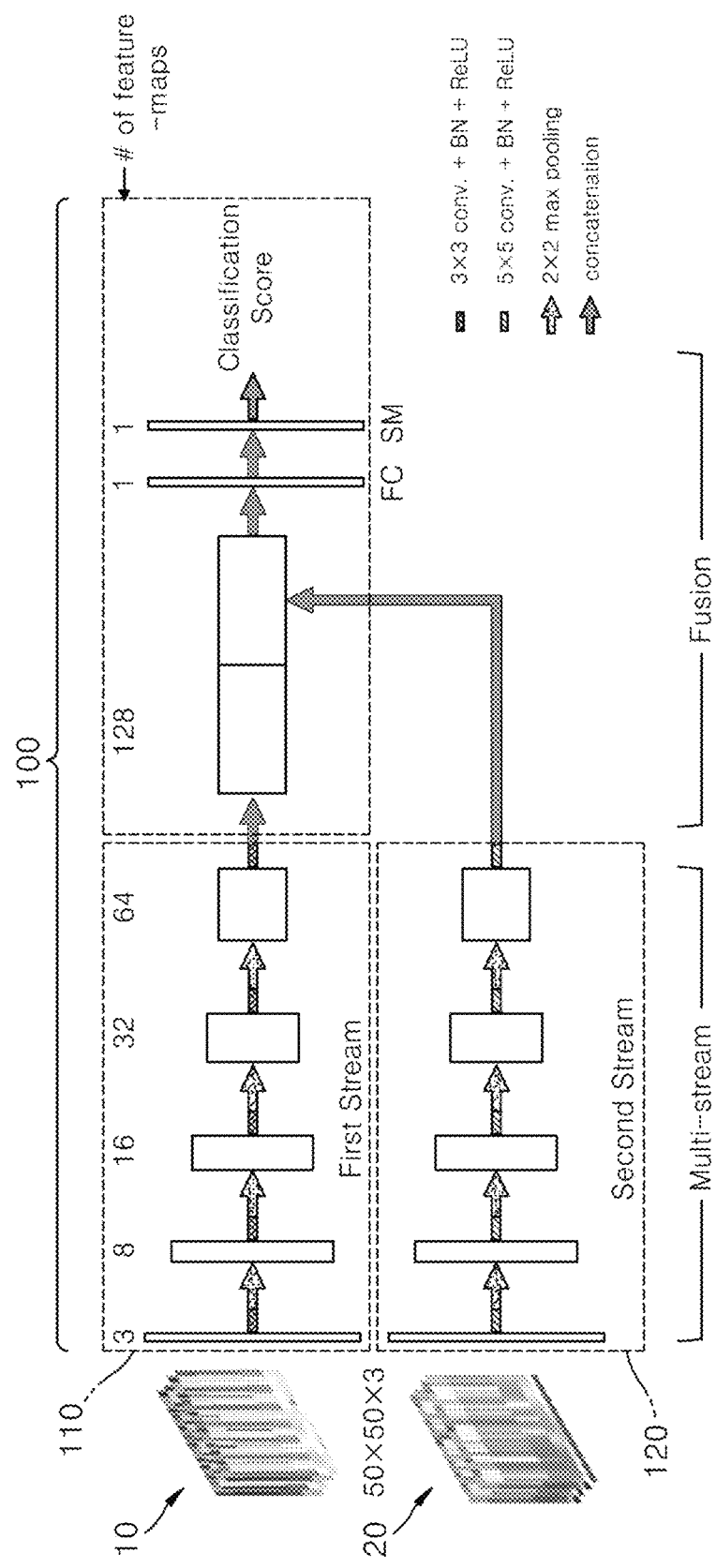
FIG. 9 is a diagram for describing an operation of a multi-stream convolutional neural network (multi-stream CNN)

FIGS. 7 and 8 are diagrams illustrating a state in which an ECG signal and an EMG signal are converted into CQT images, respectively. In addition, FIG. 9 is a diagram for describing an operation of a multi-stream convolutional neural network (multi-stream CNN).

Referring to FIG. 1, a user identification method using an ECG and an EMG according to an embodiment of the present disclosure (hereinafter, user identification method) may include acquiring one-dimensional ECG and EMG signals (S11 and S12); converting each signal into a two-dimensional image (S21 and S22); and identifying a user by inputting each image to a multi-stream convolutional neural network (multi-stream CNN) (S30).

However, the user identification method illustrated in FIG. 1 is in accordance to an embodiment, and respective steps of the present disclosure are not limited to the embodiment illustrated in FIG. 1, and some steps may be added, changed or deleted, if necessary.

The respective steps illustrated in FIG. 1 may be performed by a processor, and the processor may be implemented by including at least one physical element of application specific integrated circuits (ASICs), digital signal processors (DSPs), digital signal processing devices (DSPDs), programmable logic devices (PLDs), field programmable gate arrays (FPGAs), a controller, and microcontrollers in order to perform an operation of the present disclosure to be described below.

Hereinafter, each step illustrated in FIG. 1 will be described in detail.

The processor may acquire one-dimensional ECG and EMG signals for the user (S11 and S12).

The ECG and the EMG are one-dimensional electrical signals generated according to a contraction of the heart and a motion of the muscle, respectively, and may be measured by a current sensor and/or a voltage sensor. The sensor for detecting the ECG may be installed to contact the heart region of the user, and the sensor for detecting the EMG may be installed to contact the muscle region of the user.

The processor may perform data communication with these sensors, and may receive ECG and EMG signals from the sensors.

In one example, the present disclosure may be used for a driver authentication/identification operation, and at this time, the processor may acquire the ECG and EMG signals from sensors in the vehicle that come into contact with the user's body.

Referring to FIG. 2 as an example, each of the sensors S1 and S2 for detecting the ECG and the EMG may be installed in the vehicle and come into contact with the user's body. Specifically, the ECG detection sensor S1 and the EMG detection sensor S2 may be installed on a seat belt, respectively. The ECG detection sensor S1 may be installed to come into contact with a heart region A1 of the user when the user wears the seat belt, and the EMG detection sensor may be installed to come into contact with a muscle region A2 of the user, specifically, a trapezius region when the user wears the seat belt.

The processor may receive the ECG and EMG signals detected from each of the sensors S1 and S2 by performing data communication with each of the sensors S1 and S2. In this specification, it has been described as an example that the processor directly acquires the ECG and EMG signals from the sensors S1 and S2. However, this is only an example, and it is natural that the processor may acquire the ECG and EMG signals detected by the sensors S1 and S2 and pre-stored in a memory or a database.

Referring to FIG. 3, an ECG signal of one cycle may include a P wave, a QRS complex, and a T wave. The P wave may be generated by depolarization of the atrium, the QRS complex may be generated by depolarization of the left and right ventricles, and the T wave may be generated by repolarization of the ventricles. On the other hand, the EMG signal may be generated by depolarization and repolarization of muscle cells, and unlike the ECG signal, the EMG signal is not a signal generated according to an operation of the autonomic nervous system and thus may not have periodicity.

The processor may convert these ECG and EMG signals into two-dimensional images (S21 and S22), and may perform a preprocessing operation on the ECG and EMG signals before conversion. Hereinafter, the preprocessing method according to each embodiment will be described.

In the preprocessing according to an embodiment, the processor may normalize the ECG signal and the EMG signal at the same sampling rate.

Referring to FIG. 4 as an example, the ECG signal may be detected according to a sampling rate of 15.5 [Hz], and the EMG signal may be detected according to a sampling rate of 31 [Hz]. The processor may normalize the sampling rate of each signal in order to match the number of data included in the ECG signal and the EMG signal.

For example, the processor may normalize the sampling rate of each signal to 31 [Hz] by up-sampling the ECG signal, normalize the sampling rate of each signal to 15.5 [Hz] by down-sampling the EMG signal, and normalize the sampling rate of each signal to a random value by applying the up-sampling and/or down-sampling to each signal.

The sampling rate may determine the resolution of the images for the ECG and the EMG to be described below, and unify specifications for input data (images for the ECG and the EMG) of the multi-stream CNN 100 through the normalization operation to secure the learning consistency and efficiency of the multi-stream CNN 100.

In the preprocessing according to an embodiment, the processor may remove noise in the ECG signal and the EMG signal through a Butterworth filter. The ECG signal and the EMG signal may include noise generated inside the body or external noise according to a detection environment. The processor may remove noise through a Butterworth filter with a flat frequency response in a pass band.

Specifically, since it is known that ECG characteristics are mainly exhibited in a band of 1 to 40 [Hz], the processor may pass the ECG signal through a Butterworth band pass filter having a pass band of 1 to 40 [Hz], thereby removing noise without reflecting the ECG characteristics among the ECG signals.

Meanwhile, since it is known that EMG characteristics are mainly exhibited in a band of 50 to 100 [Hz], the processor may pass the EMG signal through a Butterworth band pass filter having a pass band of 50 to 100 [Hz], thereby removing noise without reflecting the EMG characteristics among the EMG signals.

In the preprocessing according to an embodiment, the processor may segment the ECG signal and the EMG signal by a preset time through non-fiducial segmentation.

Referring to FIG. 5 as an example, sampling rates of the ECG and EMG signals may be controlled equally through the normalization described above. In this case, the processor may segment the normalized ECG signal or EMG signal into non-fiducial segmentation. Specifically, the processor may segment each signal by a preset time (e.g., 5 seconds) regardless of the structure and characteristics of waveforms of each signal. Accordingly, the one-dimensional ECG signal and EMG signal may be segmented into signals in units of 5 seconds without a special fiducial point.

Through such non-fiducial segmentation, the ECG and EMG signals of a certain standard (e.g., 5 seconds) may be generated without any criteria, and through this, when learning a neural network model to be described below, it is possible to prevent the learning of the neural network model from being deflected.

When the above-described preprocessing is completed, the processor may convert the ECG and EMG signals into two-dimensional images, respectively (S21 and S22).

Referring to FIG. 6, the processor may convert the preprocessed ECG signal into a two-dimensional image 10, and also convert the preprocessed EMG signal into a two-dimensional image 20. Hereinafter, the two-dimensional image 10 for the ECG signal is referred to as the ECG image 10, and the two-dimensional image 20 for the EMG signal is referred to as the EMG image 20.

In the present disclosure, the two-dimensional images 10 and 20 may be expressed by a time axis and a frequency axis. Accordingly, the processor may convert the ECG and EMG signals expressed in amplitudes to the time to be expressed by the time axis and the frequency axis, and to this end, the following method may be used.

In an embodiment, the processor may convert the ECG and EMG signals into two-dimensional spectrograms. The spectrogram is an image in which a one-dimensional signal expressed in amplitudes according to the time is converted, and is expressed by the time axis and the frequency axis, but may be an image in which changes in signal amplitude according to time and frequency changes are expressed in concentration and/or color.

The processor may convert the ECG and EMG signals into the spectrograms by applying a short-time Fourier transform (STFT) to the ECG and EMG signals, and adjust the data size of the spectrogram by adjusting the conversion target time, that is, the aforementioned non-fiducial segmentation time (e.g., 5 seconds).

Referring to FIGS. 7 and 8, the processor may convert the ECG and EMG signals into spectrograms 10 and 20 by applying a constant Q-transform (CQT) instead of the STFT to the ECG and EMG signals. In this case, the spectrograms 10 and 20 vary the resolutions for each frequency band, and may express more information at a higher frequency than the conversion through STFT.

Specifically, the processor may apply the CQT to the ECG and EMG signals according to Equation 1 below, and although not expressed as Equation, the processor may additionally apply a log function to convert the spectrogram values to a decibel scale.

$$X(l, \omega) = \int_{-\infty}^{\infty} w(t, \omega) x(t + lM) e^{-i2\pi Qt} dt \quad \text{[Equation 1]}$$

(x represents a spectrogram value, ω represents each frequency, l represents a time index, w represents a window function, x represents an ECG or EMG signal, Q represents a quality factor, and M represents the number of frames to which a window is applied in the ECG or EMG signal)

Here, since the Q value is defined as a ratio of a central frequency to a frequency band, according to Equation 1, a narrow bandwidth window may be applied in a low frequency region, and a wide bandwidth window may be applied in a high frequency region. Accordingly, as illustrated in FIG. 7, the morphological features (P wave, QRS complex, and T wave) of the ECG signal may be expressed in high decibels.

That is, when the CQT is applied to the spectrogram generation, the resolution of the spectrogram, that is, the resolution may be adjusted to be suitable for natural frequency bands of the ECG and EMG signals. Accordingly, since the multi-stream CNN 100 to be described below more efficiently extracts the intrinsic features of the ECG and EMG signals from the spectrograms, the learning accuracy and learning rate of the neural network 100 may be improved.

When the ECG and EMG signals are converted into the two-dimensional images 10 and 20 according to the above-described method, the processor may identify the user by inputting the two-dimensional images 10 and 20 into the multi-stream CNN 100 (S30). Hereinafter, it is assumed that the two-dimensional images 10 and 20 input to the multi-stream CNN 100 are the spectrograms 10 and 20 converted through the CQT, and it will be described.

The multi-stream CNN 100 applied to the present disclosure may be supervised-learned by a training dataset using the ECG and EMG images 10 and 20 as input data and using user identification information as label data.

The training dataset may consist of input data and labeled output data, that is, label data. The user sets the ECG and EMG images 10 and 20 as input data and may label the user identification information corresponding to the images to generate label data.

The multi-stream CNN 100 may be supervised-learned to output label data by receiving the ECG and EMG images 10 and 20. According to the supervised-learning, parameters (weight and bias) applied to each node constituting the multi-stream CNN 100 may be learned and updated, and when the learning is completed, the multi-stream CNN 100 may receive any ECG and EMG images 10 and 20 to output user identification information corresponding to the corresponding images.

Referring to FIG. 9, the multi-stream CNN 100 according to an embodiment of the present disclosure includes a first stream neural network 110, a second stream neural network 120, and a classification neural network 130. Each of the stream neural networks 110 and 120 may include many pairs of convolutional (conv.) layers and pooling layers, and have a structure in which an output of a pair of convolutional layer and pooling layer is input to the next pair of convolutional layer and pooling layer. Meanwhile, batch normalization (BN) and rectified linear unit (ReLU) functions may be applied to the convolution layer.

The processor may input the ECG image 10 to the first stream neural network 110, and may input the EMG image 20 to the second stream neural network 120. The ECG image 10 and the EMG image 20 may be input to the first convolutional layer of each of the stream neural networks 110 and 120, and the output of the first convolutional layer may be input to the first pooling layer. The output of the first pooling layer may be input to the second convolutional layer, and the output of the second convolutional layer may be input to the second pooling layer. By repeating this process several times, the features of the ECG image and the EMG image 10 and 20 may be extracted.

The processor may concatenate the features extracted from the first and second stream neural networks 110 and 120 and identify the user based on the concatenated features.

Referring back to FIG. 9, the processor may concatenate the features extracted from the ECG image 10 with the features extracted from the EMG image 20 through the classification neural network 130, and identify the user from the concatenated features.

The classification neural network 130 may include a connection layer, a fully connected (FC) layer, and a softmax (SM) layer. The connection layer may connect a feature vector of the ECG image 10 extracted from the first stream neural network 110 with a feature vector of the EMG image 20 extracted from the second stream neural network, and for example, may connect the two feature vectors by element-wise-summing the feature vectors extracted from the stream neural networks 110 and 120 according to Equation 2 below.

$$F_{CONCAT} = 2D\_\text{Conv}(X_{CQT/ECG}) + 2D\_\text{Conv}(X_{CQT/EMG}) \quad \text{[Equation 2]}$$

($F_{CONCAT}$ represents a concatenated feature vector, $X_{CQT/ECG}$ represents an ECG image generated by CQT transformation, $X_{CQT/EMG}$ is an EMG image generated by CQT transformation, and 2D_Conv represents a function computed by a convolutional layer, batch normalization, a pooling layer, and a ReLU function)

The two concatenated feature vectors may be input to the fully connected layer, and the softmax function is applied to the output of the fully connected layer, so that a classification score may be finally output from the multi-stream CNN 100.

The classification score may be expressed as a probability for a class defined by label data, that is, user identification information, and may represent a probability for which user identification information the ECG and EMG images 10 and 20 correspond to.

The processor may identify the user based on the classification score. Specifically, the processor may extract user identification information corresponding to a maximum component in a classification score matrix, and may identify a user corresponding thereto.

Figure 10:
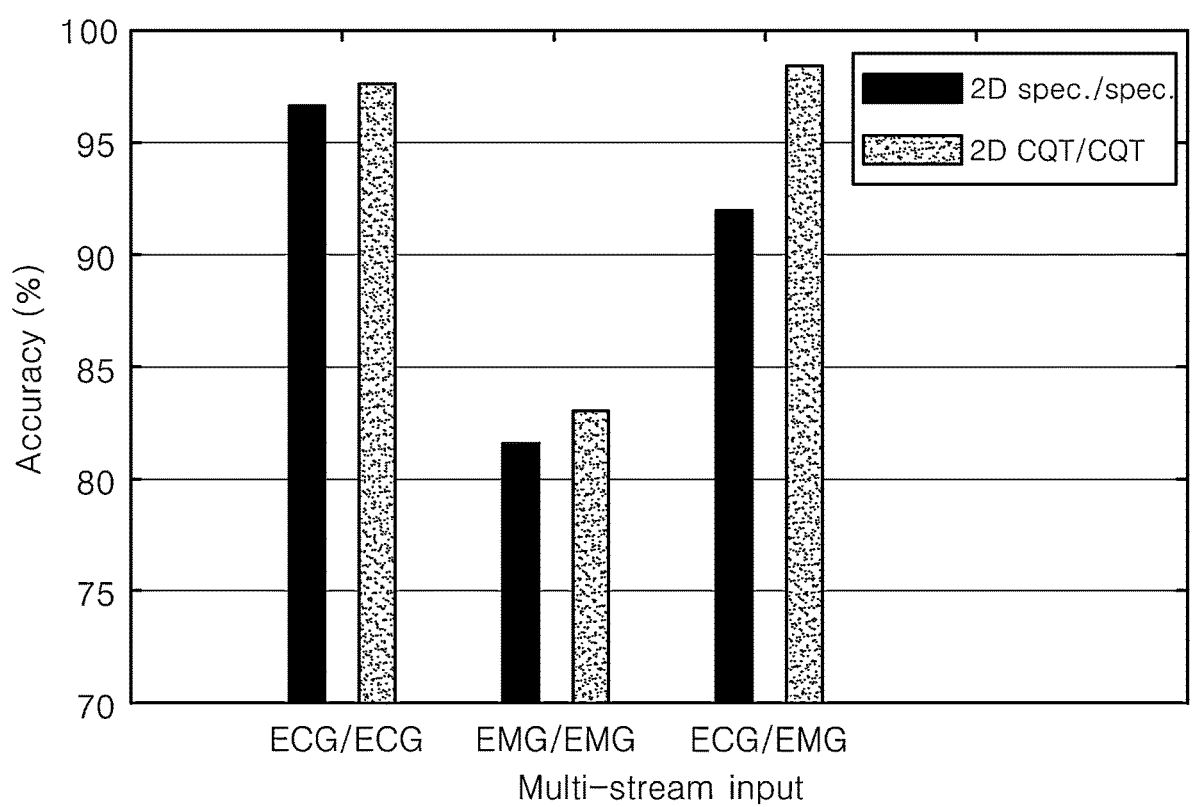
FIG. 10 is a graph illustrating user identification accuracy according to the present disclosure.

FIG. 10 is a graph illustrating identification accuracy when the present disclosure is used for an identification operation of a driver while driving a vehicle.

Referring to FIG. 10, it was confirmed that the user identification performance was improved overall by applying the CQT to spectrogram generation other than applying STFT. In particular, it can be seen that better performance is exhibited by using both ECG and EMG in all cases than using only any one signal.

As described above, according to the present disclosure, by identifying the user based on features extracted from two-dimensional images corresponding to the ECG and EMG signals, respectively, it is possible to consider not only user's unique biometric information but also motion artifacts, thereby improving the accuracy of user identification.

Further, by converting the ECG and EMG signals into the spectrograms through the CQT and identifying the user based thereon, it is possible to actively reflect morphological features of the ECG and EMG signals to neural network learning, thereby improving the accuracy of user identification.

As described above, the present disclosure has been described with reference to the illustrated drawings, but the present disclosure is not limited to the exemplary embodiments of the present disclosure and the drawings, and it will be apparent that various modifications can be made by those skilled in the art within the scope of the technical idea of the present disclosure. Further, it is natural that even through effects according to the configuration of the present disclosure are not explicitly described while describing the exemplary embodiments of the present disclosure above, expectable effects should be recognized by the configuration.

What is claimed is:

1. A user identification method using an electrocardiogram and an electromyogram comprising the steps of:
    acquiring, by a processor, one-dimensional electrocardiogram (ECG) and electromyogram (EMG) signals for a user;
    converting, by the processor, the ECG and EMG signals into two-dimensional images, respectively; and
    identifying, by the processor, a user by inputting the two-dimensional images to a multi-stream convolutional neural network (multi-stream CNN), respectively,
    wherein the multi-stream CNN is supervised-learned by a training dataset using images of the ECG and EMG signals as input data and using user identification information as label data.

2. The user identification method of claim 1, wherein the acquiring of the one-dimensional ECG and EMG signals includes acquiring the ECG and EMG signals from a sensor in a vehicle coming into contact with a user's body.

3. The user identification method of claim 1, wherein the converting of the ECG and EMG signals into the two-dimensional images, respectively includes
    normalizing the ECG signal and the EMG signal at the same sampling rate; and
    converting the normalized ECG signal and EMG signal into the two-dimensional images, respectively.

4. The user identification method of claim 1, wherein the converting of the ECG and EMG signals into the two-dimensional images, respectively includes
    removing noise in the ECG and EMG signals through a Butterworth filter; and
    converting the noise-removed ECG signal and EMG signal into the two-dimensional images, respectively.

5. The user identification method of claim 1, wherein the converting of the ECG and EMG signals into the two-dimensional images, respectively includes
    segmenting the ECG signal and the EMG signal by a preset time through non-fiducial segmentation; and
    converting the segmented ECG signal and EMG signal into the two-dimensional images, respectively.

6. The user identification method of claim 1, wherein the converting of the ECG and EMG signals into the two-dimensional images, respectively includes converting ECG and EMG signals expressed in amplitudes to the time into two-dimensional images expressed by a time axis and a frequency axis, respectively.

7. The user identification method of claim 1, wherein the converting of the ECG and EMG signals into the two-dimensional images, respectively includes converting the ECG and EMG signals into two-dimensional spectrograms.

8. The user identification method of claim 1, wherein the converting of the ECG and EMG signals into the two-dimensional images, respectively includes converting the ECG and EMG signals into two-dimensional spectrograms by applying constant Q-transform (CQT) to the ECG and EMG signals.

9. The user identification method of claim 8, wherein the converting of the ECG and EMG signals into the two-dimensional spectrograms, respectively includes converting the ECG and EMG signals into spectrograms according to Equation 1 below:

$$X(l, \omega) = \int_{-\infty}^{\infty} w(t, \omega)x(t+lM)e^{-i2\pi Qt}dt \quad \text{[Equation 1]}$$

(X represents a spectrogram value, $\omega$ represents each frequency, l represents a time index, w represents a window function, x represents an ECG or EMG signal, Q represents a quality factor, and M represents the number of frames to which a window is applied in the ECG or EMG signal).

10. The user identification method of claim 1, wherein the inputting of the two-dimensional images to the multi-stream CNN includes inputting an image for the ECG signal to a first stream neural network, and inputting an image for the EMG signal to a second stream neural network.

11. The user identification method of claim 10, wherein the identifying of the user includes concatenating features extracted from the first and second stream neural networks, respectively, and identifying the user based on the concatenated features.

12. The user identification method of claim 11, wherein the concatenating of the extracted features includes element-wise summing a feature vector extracted from the first stream neural network and the feature vector extracted from the second stream neural network.

\* \* \* \* \*